(12) United States Patent
Luan et al.

(10) Patent No.: US 12,002,549 B2
(45) Date of Patent: Jun. 4, 2024

(54) KNOWLEDGE REUSE-BASED METHOD AND SYSTEM FOR PREDICTING CELL CONCENTRATION IN FERMENTATION PROCESS

(71) Applicant: JIANGNAN UNIVERSITY, Wuxi (CN)

(72) Inventors: Xiaoli Luan, Wuxi (CN); Xiaojing Ping, Wuxi (CN); Haiying Wan, Wuxi (CN); Fei Liu, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 0 days.

(21) Appl. No.: 18/220,633

(22) Filed: Jul. 11, 2023

(65) Prior Publication Data
US 2024/0038324 A1 Feb. 1, 2024

(30) Foreign Application Priority Data
Jul. 26, 2022 (CN) .......................... 202210885437.2

(51) Int. Cl.
*G16B 5/30* (2019.01)
*C12M 1/36* (2006.01)
*G16B 40/20* (2019.01)

(52) U.S. Cl.
CPC .............. *G16B 5/30* (2019.02); *C12M 41/48* (2013.01); *G16B 40/20* (2019.02)

(58) Field of Classification Search
CPC .......... G16B 40/20; G16B 5/30; C12M 41/48; Y02P 90/30
See application file for complete search history.

(56) References Cited

U.S. PATENT DOCUMENTS

| | | | | |
|---|---|---|---|---|
| 8,818,562 | B2* | 8/2014 | Bluck | C12M 41/00 436/24 |
| 9,037,298 | B2* | 5/2015 | Macharia | G05B 13/04 700/270 |
| 9,046,882 | B2* | 6/2015 | Bartee | C12M 21/12 |
| 10,261,479 | B2* | 4/2019 | Krasberg | G05B 13/024 |
| 2013/0029314 | A1* | 1/2013 | Rostalski | C12M 21/04 435/286.7 |
| 2013/0029315 | A1* | 1/2013 | Rostalski | C12M 41/42 435/286.7 |

* cited by examiner

*Primary Examiner* — Shogo Sasaki
(74) *Attorney, Agent, or Firm* — SZDC Law PC

(57) ABSTRACT

The present invention provides a knowledge reuse-based method and system for predicting a cell concentration in a fermentation process. The method includes: constructing a cell concentration soft sensor universal model in a fermentation process; acquiring and preprocessing process data of a fermentation stage A; determining a cell concentration soft sensor model of the fermentation stage A; designing a cell concentration online soft sensor of a fermentation stage B; and predicting a cell concentration of the fermentation stage B according to the cell concentration online soft sensor of the fermentation stage B. The present invention resolves the problems of weak generalization of a cell concentration soft sensor model and high costs of establishing models for fermentation stages separately, thereby improving the prediction accuracy of a cell concentration soft sensor.

9 Claims, 5 Drawing Sheets

KNOWLEDGE REUSE-BASED METHOD AND SYSTEM FOR PREDICTING CELL CONCENTRATION IN FERMENTATION PROCESS

This application claims priority to Chinese Patent Application No. 202210885437.2, filed on Jul. 26, 2022, which is incorporated by reference for all purposes as if fully set forth herein.

FIELD OF THE INVENTION

The present invention relates to the field of biological technologies and soft measurement technologies, and specifically to a knowledge reuse-based method and system for predicting a cell concentration in a fermentation process.

DESCRIPTION OF THE RELATED ART

In an existing fermentation process, due to the lack of biosensors or the complexity of the process, the online measurement of key variables is an important basis for improving product yields and enhancing product quality. A cell concentration in the fermentation process shows obvious multi-stage characteristics throughout the fermentation process. There are differences in the dynamic characteristics of various stages. The use of only a single soft sensor leads to reduced model generalization, and it is costly to establish models for the stages separately.

SUMMARY OF THE INVENTION

Embodiments of the present invention provide a knowledge reuse-based method and system for predicting a cell concentration in a fermentation process, to resolve the problems of weak generalization of a cell concentration soft sensor model and high costs of establishing models for fermentation stages separately in the prior art.

Embodiments of the present invention provide a knowledge reuse-based method for predicting a cell concentration in a fermentation process. The method includes:

S1: constructing a cell concentration soft sensor universal model in a fermentation process, where the fermentation process is divided into four stages in time order: a lag phase, an exponential growth phase, a stationary phase, and a decline phase, and for two stages that occur successively, it is defined that a former stage is a fermentation stage A and a latter stage is a fermentation stage B;

S2: acquiring and preprocessing process data of the fermentation stage A;

S3: determining a cell concentration soft sensor model of the fermentation stage A based on the cell concentration soft sensor universal model in combination with a process data result of the fermentation stage A after the preprocessing;

S4: acquiring process data of the fermentation stage B, and after preprocessing, designing a cell concentration online soft sensor of the fermentation stage B with the cell concentration soft sensor model of the fermentation stage A; and S5: predicting a cell concentration of the fermentation stage B according to the cell concentration online soft sensor of the fermentation stage B, where a method for designing a cell concentration online soft sensor of the fermentation stage B in step S4 is:

S41: setting a parameter estimation of the cell concentration soft sensor model of the fermentation stage B to:

$$\hat{\theta}_{k+\tau+1} = \hat{\theta}_A + \hat{H}_{k+\tau+1} E_{k+\tau+1},$$

where $$E_{k+\tau+1} = Y_{k+\tau+1} - X_{k+\tau+1} \hat{\theta}_A,$$

$$Y_{k+\tau+1} = [y_{1+\tau}, y_{2+\tau} \ldots, y_{k+\tau}, y_{k+\tau+1}]^T = [Y_{k+\tau}; y_{k+\tau+1}],$$

$$X_{k+\tau+1} = \begin{bmatrix} -y_\tau & \cdots & -y_{\tau-p} & u_1 & \cdots & u_{1-q} \\ -y_{1+\tau} & \cdots & -y_{1+\tau-p} & u_2 & \cdots & u_{2-q} \\ \vdots & \ddots & \vdots & \vdots & \ddots & \vdots \\ -y_{k-1+\tau} & \cdots & -y_{k-1+\tau} & u_k & \cdots & u_{k-q} \\ -y_{k+\tau} & \cdots & -y_{k+\tau-p} & u_{k+1} & \cdots & u_{k+1-q} \end{bmatrix} = [X_{k+\tau}; x_{k+\tau+1}^T],$$

where at a moment $k+\tau+1$, for the cell concentration soft sensor model of the fermentation stage B, a delay is $\tau_B = \tau_A$, orders are $p_B = p_A$ and $q_B = q_A$, the parameter estimation is $\hat{\theta}_{k+\tau+1} = [\hat{a}_1, \ldots, \hat{a}_{p_B}, \hat{b}_1, \ldots, \hat{b}_{q_B}]^T$, $\hat{\theta}_A$ is a parameter estimation of the fermentation stage A, $\hat{H}_{k+\tau+1}$ is a gain matrix of the cell concentration soft sensor model of the fermentation stage B at the moment $k+\tau+1$, $E_{k+\tau+1}$ is an innovation vector at the moment $k+\tau+1$, $Y_{k+\tau+1}$ is a cell concentration matrix of the fermentation stage B at the moment $k+\tau+1$, and $X_{k+\tau+1}$ is an input matrix of the fermentation stage B at the moment $k+\tau+1$;

S42: calculating the gain matrix $\hat{H}_{k+\tau+1}$ of the cell concentration soft sensor model of the fermentation stage B in step S41;

S43: designing the cell concentration online soft sensor of the fermentation stage B based on a parameter estimation vector $\hat{\theta}_{k+\tau+1}$ and the gain matrix $\hat{H}_{k+\tau+1}$ of the cell concentration soft sensor model of the fermentation stage B.

Preferably, a method for constructing a cell concentration soft sensor universal model in a fermentation process in step S1 includes:

S11: selecting a dilution ratio as an auxiliary variable based on dynamic characteristics of the fermentation process, and setting the cell concentration soft sensor model to:

$$y_{k+\tau} + a_1 y_{k+\tau-1} + \cdots + a_p y_{k+\tau-p} = b_0 u_k + b_1 u_{k-1} + \cdots + b_q u_{k-q} + v_{k+\tau},$$

where k is a moment, $\tau$ is the delay of the soft sensor model, p and q are the orders of the soft sensor model, a and b are coefficients, $y_{k+\tau}$ is a cell concentration at a moment $k+\tau$, $u_k$ is an auxiliary variable at the moment k, $v_{k+\tau}$ is a cell concentration measurement noise at the moment $k+\tau$, and a type of the noise is selected from white noises satisfying Gaussian distribution, t distribution, and Poisson distribution; and S12: performing vector transformation on the cell concentration soft sensor model, to obtain the cell concentration soft sensor universal model:

$$y_{k+\tau} = x_{k+\tau}^T \theta + v_{k+\tau},$$

where an input vector is $x_{k+\tau} = [y_{k+\tau-1} \ y_{k+\tau-2} \ \ldots \ y_{k+\tau-p} \ u_k \ \ldots \ u_{k-q}]^T$, and a parameter is $\theta = [a_1, \ldots, a_p, b_0, \ldots, b_q]^T$.

Preferably, a method for preprocessing process data of the fermentation stage A in step S2 is:

eliminating a nonnumerical sample point in the process data of the fermentation stage A, and eliminating abnormal working condition data according to a working condition record; eliminating an outlier in the process data of the fermentation stage A; filling a missing value in the process data of the fermentation stage A; and removing a dimensional difference between an auxiliary variable and a quality variable in the fermentation stage A.

Preferably, a method for calculating the gain matrix $\hat{H}_{k+\tau+1}$ of the cell concentration soft sensor model of the fermentation stage B includes:

step 1: defining a loss function of a knowledge reuse-based soft sensor model:

$$J=\text{trace}\{E[(\theta_B-\hat{\theta}_{k+\tau+1})(\theta_B-\hat{\theta}_{k+\tau+1})^T]\},$$

where $\theta_B$ is an actual parameter value of the fermentation stage B, $\hat{\theta}_{k+\tau+1}$ is the parameter estimation of the fermentation stage B at the moment $k+\tau+1$, $E[\cdot]$ is an averaging operation, $\text{trace}\{\cdot\}$ is a trace operation of a matrix, J is a loss function with respect to $\hat{H}_{k+\tau+1}$; and step 2: calculating the gain matrix $\hat{H}_{k+\tau+1}$ based on a method of minimizing the loss function:

$$\hat{H}_{k+\tau+1}=(F_{k+\tau+1}+\hat{D}_{k+\tau+1}^{-1})^{-1}X_{k+1}^T\Sigma_{k+1}^{-1},$$

where $F_{k+\tau+1}=X_{k+1}\Sigma_{k+\tau+1}^{-1}X_{k+1}$, $\hat{D}_{k+\tau+1}^{-1}=\hat{d}_{k+\tau+1}\hat{d}_{k+\tau+1}^T$, $X_{k+1}^T\hat{d}_{k+\tau+1}=E_{k+\tau+1}$, $F_{k+\tau+1}$ is a Fisher information matrix of the soft sensor model of the fermentation stage B at the moment $k+\tau+1$, $\Sigma_{k+1}^{-1}$ is an inverse of a measurement noise covariance matrix of the fermentation stage B at a moment $k+1$, $\hat{D}_{k+\tau+1}^{-1}$ is a difference covariance matrix between the fermentation stage A and the fermentation stage B at the moment $k+\tau+1$, and $\hat{d}_{k+\tau+1}$ is a parameter difference between the fermentation stage A and the fermentation stage B at the moment $k+\tau+1$.

Preferably, a method for designing the online soft sensor based on a parameter estimation vector $\hat{\theta}_{k+\tau+1}$ and the gain matrix $\hat{H}_{k+\tau+1}$ of the cell concentration soft sensor model of the fermentation stage B includes:

step 1: initializing $\hat{d}_0$, $G_0$, and $Q_0$ at an initial moment of the fermentation stage B;

where $\hat{d}$ is a model parameter difference between the fermentation stage A and the fermentation stage B, $\hat{d}_0$ and $G_0$ are $(p_B+q_B)$-dimensional zero vectors, and $Q_0$ is a $(p_B+q_B)\times(p_B+q_B)$-dimensional zero matrix;

step 2: solving the cell concentration online soft sensor of the fermentation stage B, specifically denoted as follows:

$$\hat{\theta}_{k+\tau+1}=\hat{\theta}_A+P_{k+\tau+1}G_{k+\tau+1},$$

where $$F_{k+\tau+1}=F_{k+\tau}+\sigma_{k+1}^{-2}x_{k+\tau+1}x_{k+\tau+1}^T=Q_{k+\tau}+f_{k+\tau+1},$$

$$G_{k+\tau+1}=G_{k+\tau}+\sigma_{k+\tau+1}^{-2}x_{k+\tau+1}(y_{k+\tau+1}-x_{k+\tau+1}^T\hat{\theta}_A)=G_{k+\tau}+g_{k+\tau+1},$$

$$P_{k+\tau+1}\leq(F_{k+\tau+1}+\hat{D}_{k+\tau+1}^{-1})^{-1},$$

$\hat{\theta}_A$ is the parameter estimation of the fermentation stage A, $\hat{\theta}_{k+\tau+1}$ is the parameter estimation of the fermentation stage B at the moment $k+\tau+1$, $\sigma_{k+\tau+1}^{-2}$ is a measurement noise variance of a cell concentration of the fermentation stage B at the moment $k+\tau+1$, $x_{k+\tau+1}$ is an input vector of the fermentation stage B at the moment $k+\tau+1$, $y_{k+\tau+1}$ is a cell concentration of the fermentation stage B at the moment $k+\tau+1$, and when new measurement data is acquired, $F_{k+\tau+1}$ has updated data quality of the fermentation stage B, and $G_{k+\tau+1}$ and $P_{k+\tau+1}$ have updated a difference between the fermentation stages A and B; and step 3: before the fermentation stage B ends, when new measurement data is acquired, sequentially calculating $F_{k+\tau+1}$, $G_{k+\tau+1}$, and $P_{k+\tau+1}$, and updating a parameter $\hat{\theta}_{k+\tau+1}$ of the soft sensor model.

Preferably, a method for predicting a cell concentration of the fermentation stage B according to the cell concentration soft sensor of the fermentation stage B in step S5 is:

introducing the parameter estimation $\hat{\theta}_{k+\tau+1}$ of the soft sensor into the soft sensor universal model $y_{k+\tau}=x_{k+\tau}^T\theta+v_{k+\tau}$, to obtain a predicted cell concentration value $\hat{y}_{k+\tau+1}$ of the fermentation stage B:

$$\hat{y}_{k+\tau+1}=\hat{x}_{k+\tau+1}\hat{\theta}_{k+\tau+1}.$$

Preferably, the method of minimizing the loss function is selected from a feasible direction method, a quadratic programming method, a particle swarm algorithm, Bayesian optimization, and a random search and gradient descent method.

Preferably, a method for calculating the inverse of the noise covariance matrix is selected from a Kalman filter and an extended form thereof, statistical hypothesis testing, and regression analysis.

Preferably, a method for calculating the model parameter difference d between the fermentation stage A and the fermentation stage B is selected from a recursive least squares method, a recursive extended least squares method, a recursive maximum likelihood method, a random Newton method, Kalman estimation, a prediction error method, and a long short-term memory network.

Embodiments of the present invention further provide a knowledge reuse-based system for predicting a cell concentration in a fermentation process. The system includes:

a soft sensor universal model construction unit, configured to construct a cell concentration soft sensor universal model in a fermentation process, where the fermentation process is divided into four stages in time order: a lag phase, an exponential growth phase, a stationary phase, and a decline phase, and for two stages that occur successively, it is defined that a former stage is a fermentation stage A and a latter stage is a fermentation stage B;

a data acquisition and preprocessing unit, configured to acquire and preprocess process data of the fermentation stage A;

a fermentation stage A-soft sensor model determination unit, configured to determine a cell concentration soft sensor model of the fermentation stage A based on the cell concentration soft sensor universal model in combination with a process data result of the fermentation stage A after the preprocessing;

a fermentation stage B-soft sensor design unit, configured to acquire process data of the fermentation stage B, and after preprocessing, design a cell concentration online soft sensor of the fermentation stage B with the cell concentration soft sensor model of the fermentation stage A; and a cell concentration prediction unit, configured to predict a cell concentration of the fermentation stage B according to the cell concentration online soft sensor of the fermentation stage B.

As can be seen from the foregoing technical solutions, the application of the present invention has the following advantages:

The embodiments of the present invention provide a knowledge reuse-based method and system for predicting a cell concentration in a fermentation process. In the present invention, dynamic characteristics of a fermentation process and a detection delay of a cell concentration are taken into consideration, and at the same time a cell concentration online soft sensor of a next stage is designed by using a knowledge reuse technology and relying on a soft sensor model of a former stage in the fermentation process, to resolve the problems of weak generalization of a cell concentration soft sensor model and high costs of establishing models for fermentation stages separately, thereby improving the prediction accuracy of a cell concentration soft sensor.

BRIEF DESCRIPTION OF THE DRAWINGS

To describe the technical solutions in the embodiments of the present invention or in the prior art more clearly, the accompanying drawings that need to be used in the embodiments are briefly described below. The features and advantages of the present invention will be more clearly understood by referring to the accompanying drawings, which are schematic and should not be construed as limiting the present invention in any way. A person of ordinary skill in the art can obtain other accompanying drawings without creative efforts based on these accompanying drawings. Where.

DETAILED DESCRIPTION OF THE PREFERRED EMBODIMENTS

To make the objectives, technical solutions, and advantages of the embodiments of the present invention clearer, the following clearly and completely describes the technical solutions in embodiments of the present invention with reference to the accompanying drawings in embodiments of the present invention. Apparently, the described embodiments are some rather than all of the embodiments of the present invention. All other embodiments obtained by persons of ordinary skill in the art based on the embodiments of the present invention without creative efforts shall fall within the protection scope of the present invention.

Embodiment 1

Figure 1:
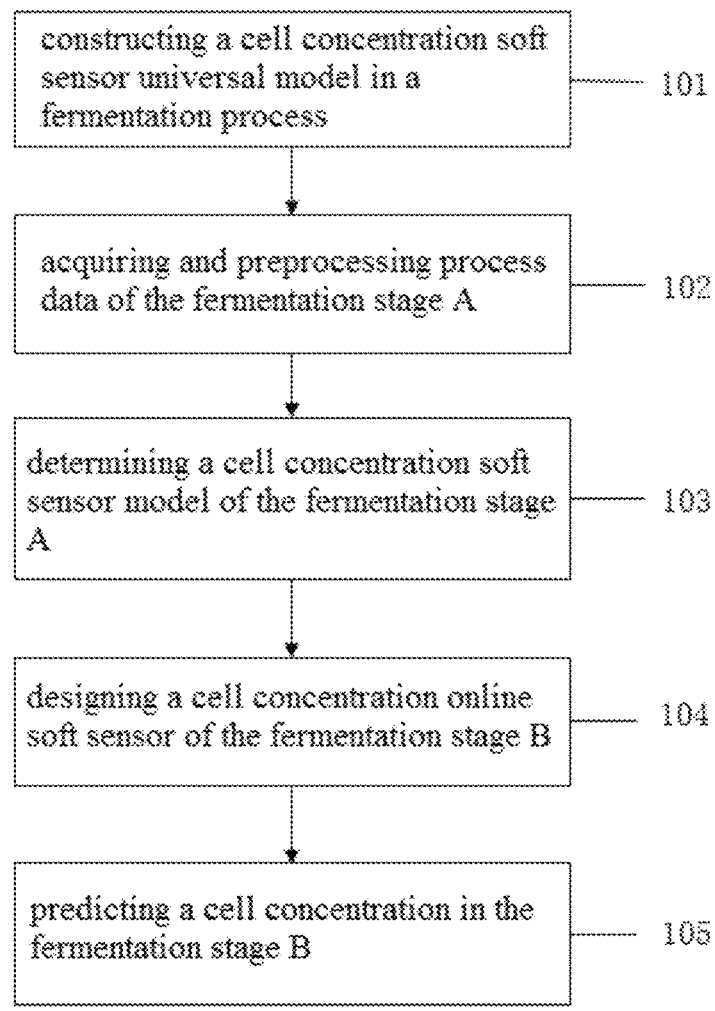
FIG. 1 is a flowchart of a knowledge reuse-based method for predicting a cell concentration in a fermentation process according to an embodiment of the present invention.

Embodiments of the present invention provide a knowledge reuse-based method for predicting a cell concentration in a fermentation process. As shown in FIG. 1, the method includes the following steps.

S101: Construct a cell concentration soft sensor universal model in a fermentation process, where the fermentation process is divided into four stages in time order: a lag phase, an exponential growth phase, a stationary phase, and a decline phase, and for two stages that occur successively, it is defined that a former stage is a fermentation stage A and a latter stage is a fermentation stage B.

S102: Acquire and preprocess process data of the fermentation stage A.

S103: Determine a cell concentration soft sensor model of the fermentation stage A based on the cell concentration soft sensor universal model in combination with a process data result of the fermentation stage A after the preprocessing.

S104: Acquire process data of the fermentation stage B, and after preprocessing, design a cell concentration online soft sensor of the fermentation stage B with the cell concentration soft sensor model of the fermentation stage A.

S105: Predict a cell concentration of the fermentation stage B according to the cell concentration online soft sensor of the fermentation stage B.

A method for designing a cell concentration online soft sensor of the fermentation stage B in step S104 is:

S1041: Set a parameter estimation of the cell concentration soft sensor model of the fermentation stage B to:

$$\hat{\theta}_{k+\tau+1} = \hat{\theta}_A + \hat{H}_{k+\tau+1} E_{k+\tau+1},$$

where $$E_{k+\tau+1} = Y_{k+\tau+1} - X_{k+\tau+1} \hat{\theta}_A,$$

$$Y_{k+\tau+1} = [y_{1+\tau}, y_{2+\tau} \ldots, y_{k+\tau}, y_{k+\tau+1}]^T = [Y_{k+\tau}; y_{k+\tau+1}],$$

$$X_{k+\tau+1} = \begin{bmatrix} -y_\tau & \cdots & -y_{\tau-p} & u_1 & \cdots & u_{1-q} \\ -y_{1+\tau} & \cdots & -y_{1+\tau-p} & u_2 & \cdots & u_{2-q} \\ \vdots & \ddots & \vdots & \vdots & \ddots & \vdots \\ -y_{k-1+\tau} & \cdots & -y_{k-1+\tau} & u_k & \cdots & u_{k-q} \\ -y_{k+\tau} & \cdots & -y_{k+\tau-p} & u_{k+1} & \cdots & u_{k+1-q} \end{bmatrix} = [X_{k+\tau}; x_{k+\tau+1}^T],$$

where at a moment k+τ+1, for the cell concentration soft sensor model of the fermentation stage B, a delay is $\tau_B = \tau_A$, orders are $p_B = p_A$ and $q_B = q_A$, the parameter estimation is $\hat{\theta}_{k+\tau+1} = [\hat{a}_1, \ldots, \hat{a}_{p_B}, \hat{b}_1, \ldots, \hat{b}_{q_B}]^T$, $\hat{\theta}_A$ is a parameter estimation of the fermentation stage A, $\hat{H}_{k+\tau+1}$ is a gain matrix of the cell concentration soft sensor model of the fermentation stage B at the moment k+τ+1, $E_{k+\tau+1}$ is an innovation vector at the moment k+τ+1, $Y_{k+\tau+1}$ is a cell concentration matrix of the fermentation stage B at the moment k+τ+1, and $X_{k+\tau+1}$ is an input matrix of the fermentation stage B at the moment k+τ+1.

S1042: Calculate the gain matrix $\hat{H}_{k+\tau+1}$ of the cell concentration soft sensor model of the fermentation stage B in step S41.

S1043: Design the cell concentration online soft sensor of the fermentation stage B based on a parameter estimation vector $\hat{\theta}_{k+\tau+1}$ and the gain matrix $\hat{H}_{k+\tau+1}$ of the cell concentration soft sensor model of the fermentation stage B.

The embodiments of the present invention provide a knowledge reuse-based method and system for predicting a cell concentration in a fermentation process. Based on, in the present invention, dynamic characteristics of a fermentation process and a detection delay of a cell concentration are taken into consideration, and at the same time a cell concentration online soft sensor of a next stage is designed by using a knowledge reuse technology and relying on a soft sensor model of a former stage in the fermentation process, to resolve the problems of weak generalization of a cell concentration soft sensor model and high costs of establishing models for fermentation stages separately, thereby improving the prediction accuracy of a cell concentration soft sensor.

Further, a method for constructing a cell concentration soft sensor universal model in a fermentation process in step S101 is:

S1011: Select a dilution ratio as an auxiliary variable based on dynamic characteristics of the fermentation process, and setting the cell concentration soft sensor model to:

$$y_{k+\tau}+a_1 y_{k+\tau-1}+\cdots+a_p y_{k+\tau-p}=b_0 u_k + b_1 u_{k-1}+\cdots+b_q u_{k-q}+v_{k+\tau},$$

where k is a moment, $\tau$ is the delay of the soft sensor model, p and q are the orders of the soft sensor model, a and b are coefficients, $y_{k+\tau}$ is a cell concentration at a moment k+E, $u_k$ is an auxiliary variable at the moment k, $v_{k+\tau}$ is a cell concentration measurement noise at the moment k+$\tau$, and a type of the noise is selected from white noises satisfying Gaussian distribution, t distribution, and Poisson distribution.

S1012: Perform vector transformation on the cell concentration soft sensor model, to obtain the cell concentration soft sensor universal model:

$$y_{k+\tau}=x_{k+\tau}^T\theta+v_{k+\tau},$$

where an input vector is $x_{k+\tau}=[y_{k+\tau-1}\ y_{k+\tau-2}\ \cdots\ y_{k+\tau-p}\ u_k\ \cdots\ u_{k-q}]^T$, and a parameter is $\theta=[a_1,\cdots,a_p, b_0,\cdots,b_q]^T$.

Further, a method for preprocessing process data of the fermentation stage in step S102 includes:
- eliminating a nonnumerical sample point in the process data of the fermentation stage;
- eliminating an outlier in the process data of the fermentation stage, where a method for eliminating an outlier in the process data of the fermentation stage is selected from cluster analysis, three-sigma rule of thumb, a nearest neighbors method, and box plot analysis;
- filling a missing value in the process data of the fermentation stage, where a method for filling a missing value in the process data of the fermentation stage is selected from average filling, median filling, mode filling, and machine learning algorithm filling; and
- removing a dimensional difference between an auxiliary variable and a quality variable in the fermentation stage, where a method for removing a dimensional difference between an auxiliary variable and a quality variable in the fermentation stage is any one of normalization, z-score standardization, centralization, Hellinger transformation, and Pareto standardization.

Figure 2:
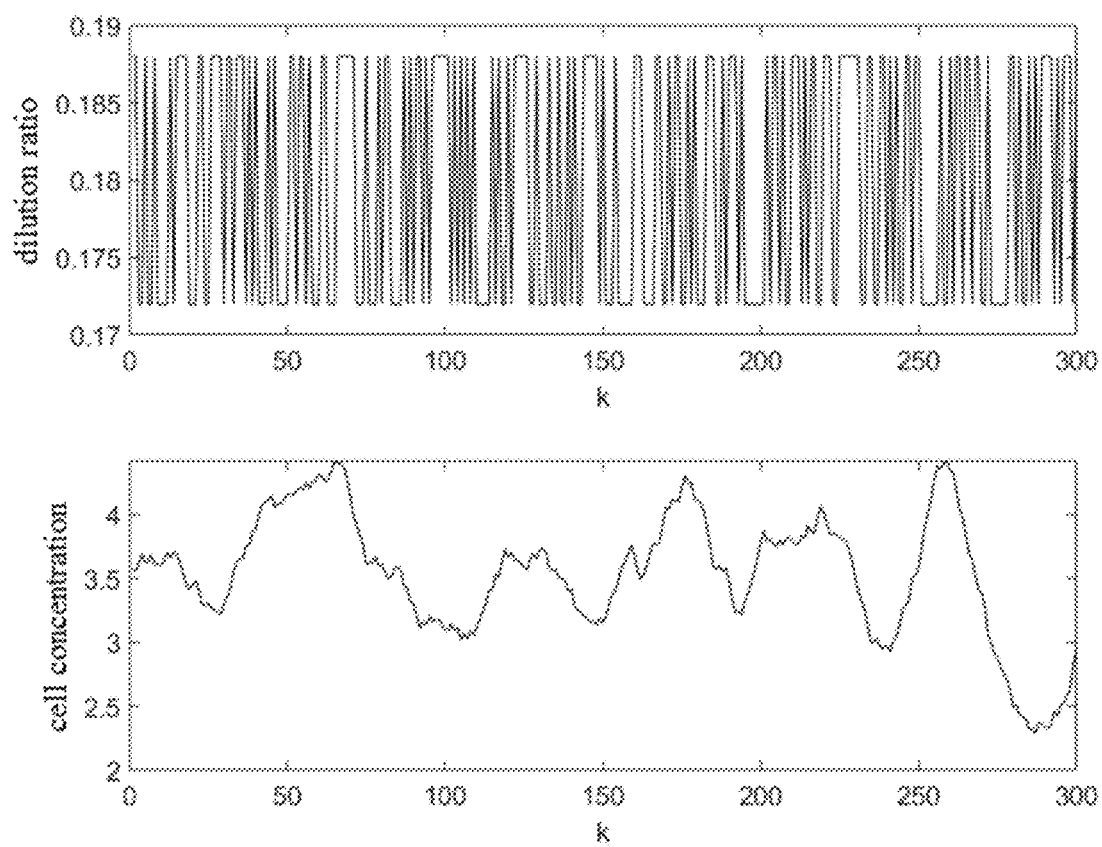
FIG. 2 shows data curves of a dilution ratio and a cell concentration of a fermentation stage A.

Data of a dilution ratio and a cell concentration is obtained after the process data of the fermentation stage A is processed, as shown in FIG. 2.

Figure 3:
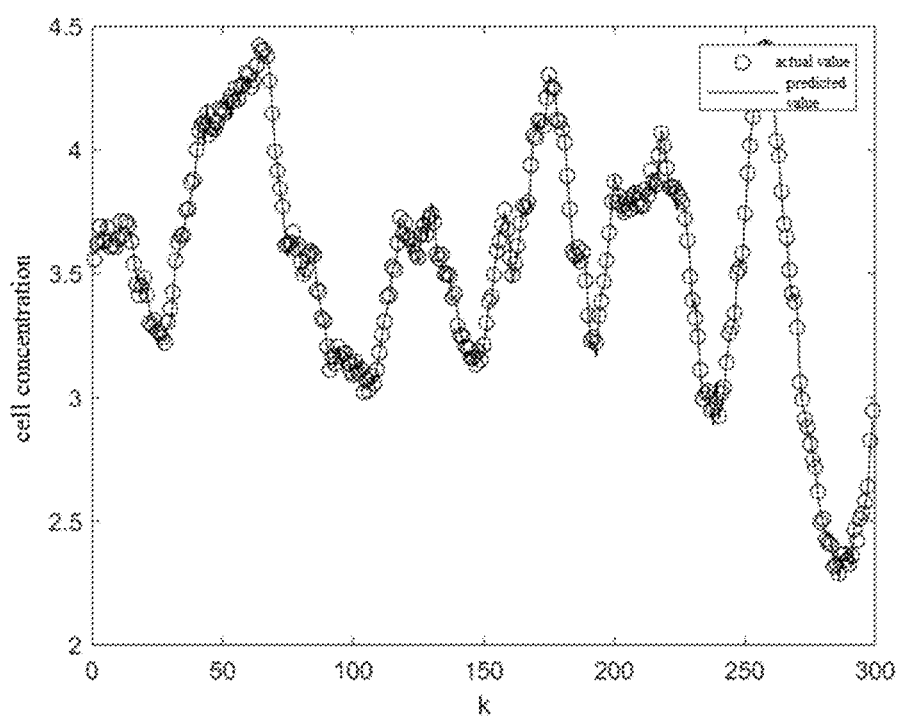
FIG. 3 shows a predicted curve of a cell concentration of a fermentation stage A.

Further, the delay $\tau_A$, the orders $p_A$ and $q_A$, and the parameter $\theta_A$ of the cell concentration soft sensor model of the fermentation stage A are determined according to the preprocessed result of the process data of the fermentation stage A based on the cell concentration soft sensor universal model in step S103, so that a predicted result of the cell concentration of the fermentation stage A may be obtained, as shown in FIG. 3.

A method for determining the delay of the cell concentration soft sensor model of the fermentation stage A is any one of mechanism analysis, experimental study, and an approximation technique.

A method for determining the orders of the cell concentration soft sensor model of the fermentation stage A is any one of a Hankel matrix method, an AIC criterion ordering method, a BIC criterion ordering method, an FPE criterion ordering method, residual method, and F-test method.

A method for determining the parameter of the cell concentration soft sensor model of the fermentation stage A is any one of least squares estimation, maximum likelihood estimation, a prediction error method, a random approximation method, support vector regression, partial least squares, and a neural network.

Figure 4:
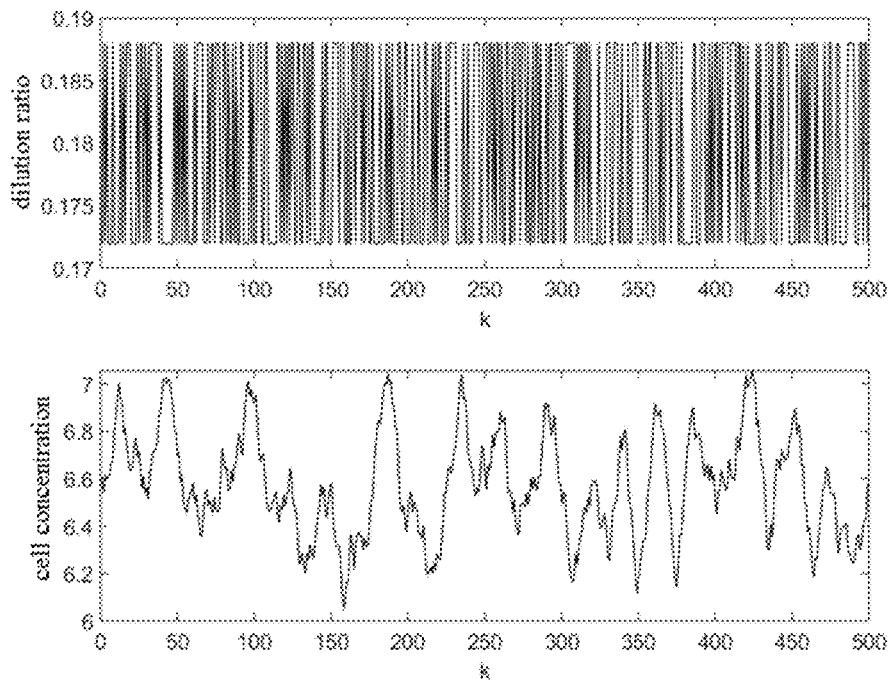
FIG. 4 shows data curves of a dilution ratio and a cell concentration of a fermentation stage B.

Further, after the fermentation stage A is completed and the fermentation stage B has started, the process data of the fermentation stage B is acquired and preprocessed, to obtain processed data of the dilution ratio and the cell concentration, as shown in FIG. 4.

Figure 5:
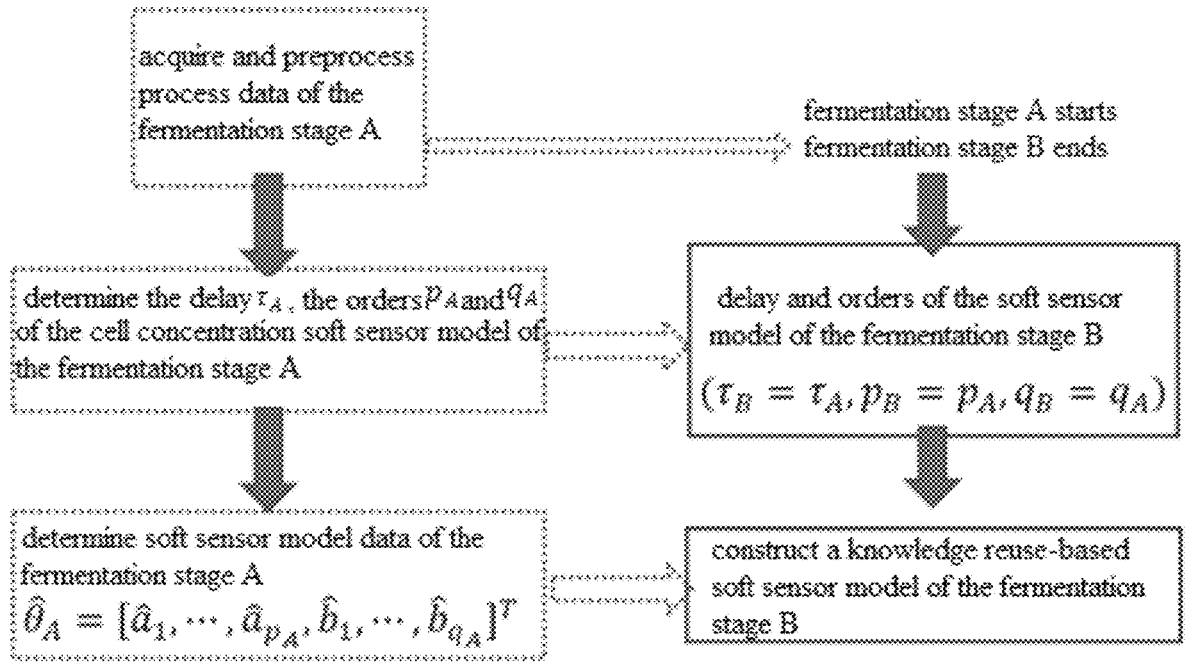
FIG. 5 is a schematic diagram of a method for constructing a knowledge reuse-based soft sensor of a fermentation stage B according to an embodiment.

Further, a method for designing a cell concentration soft sensor of the fermentation stage B in step S104 includes: constructing a knowledge reuse-based soft sensor of the fermentation stage B according to the data of the cell concentration soft sensor model of the fermentation stage A, as shown in FIG. 5, specifically including the following steps:

S1041: Set a parameter estimation of the cell concentration soft sensor model of the fermentation stage B to:

$$\hat{\theta}_{k+\tau+1} = \hat{\theta}_A + \hat{H}_{k+\tau+1} E_{k+\tau+1},$$

where $$E_{k+\tau+1} = Y_{k+\tau+1} - X_{k+\tau+1}\hat{\theta}_A,$$

$$Y_{k+\tau+1} = [y_{1+\tau}, y_{2+\tau} \ldots, y_{k+\tau}, y_{k+\tau+1}]^T = [Y_{k+\tau}; y_{k+\tau+1}],$$

$$X_{k+\tau+1} = \begin{bmatrix} -y_\tau & \cdots & -y_{\tau-p} & u_1 & \cdots & u_{1-q} \\ -y_{1+\tau} & \cdots & -y_{1+\tau-p} & u_2 & \cdots & u_{2-q} \\ \vdots & \ddots & \vdots & \vdots & \ddots & \vdots \\ -y_{k-1+\tau} & \cdots & -y_{k-1+\tau} & u_k & \cdots & u_{k-q} \\ -y_{k+\tau} & \cdots & -y_{k+\tau-p} & u_{k+1} & \cdots & u_{k+1-q} \end{bmatrix} = [X_{k+\tau}; x_{k+\tau+1}^T],$$

where at a moment k+$\tau$1, for the cell concentration soft sensor model of the fermentation stage B, a delay is $\tau_B=\tau_A$, orders are $p_B=p_A$ and $q_B=q_A$, the parameter estimation is $\hat{\theta}_{k+\tau+1}=[\hat{a}_1,\ldots,\hat{a}_{p_B},\hat{b}_1,\ldots,\hat{b}_{q_B}]^T$, $\hat{\theta}_A$ is a parameter estimation of the fermentation stage $\hat{H}_{k+\tau+1}$ is a gain matrix of the cell concentration soft sensor model of the fermentation stage B at the moment k+$\tau$1, $E_{k+\tau+1}$ is an innovation vector at the moment k+$\tau$+1, $Y_{k+\tau+1}$ is a cell concentration matrix of the fermentation stage B at the moment k+$\tau$1, and $X_{k+\tau+1}$ is an input matrix of the fermentation stage B at the moment k+$\tau$1.

S104: Calculate the gain matrix $\hat{H}_{k+\tau+1}$ of the cell concentration soft sensor model of the fermentation stage B in step S1041.

S1043: Design the cell concentration online soft sensor of the fermentation stage B based on a parameter estimation vector $\hat{\theta}_{k+\tau+1}$ and the gain matrix $\hat{H}_{k+\tau+1}$ of the cell concentration soft sensor model of the fermentation stage B.

A method for calculating the gain matrix $\hat{H}_{k+\tau+1}$ of the cell concentration soft sensor model of the fermentation stage B in step S1042 includes:

step 1: defining a loss function of a knowledge reuse-based soft sensor model:

$$J=\text{trace}\{E[(\theta_B-\hat{\theta}_{k+\tau+1})(\theta_B-\hat{\theta}_{k+\tau+1})^T]\},$$

where $\theta_B$ is an actual parameter value of the fermentation stage B, $\hat{\theta}_{k+\tau+1}$ is the parameter estimation of the fermentation stage B at the moment k+$\tau$1, E[•] is an averaging operation, trace{•} is a trace operation of a matrix, J is a loss function with respect to $\hat{H}_{k+\tau+1}$; and step 2: calculating the gain matrix $\hat{H}_{k+\tau+1}$ based on a method of minimizing $$\hat{H}_{k+\tau+1}=(F_{k+\tau+1}+\hat{D}_{k+\tau+1})^{-1}X_{k+1}{}^T\Sigma_{k+1}{}^{-1},$$

where $F_{k+\tau+1}=X_{k+1}{}^T\Sigma_{k+\tau+1}{}^{-1}X_{k+1}$, $\hat{D}_{k+\tau+1}{}^{-1}=\hat{d}_{k+\tau+1}$ $\hat{d}_{k+\tau+1}{}^T$, $$X_{k+1}{}^T\hat{d}_{k+\tau+1}=E_{k+\tau+1},$$

$F_{k+\tau+1}$ is a Fisher information matrix of the soft sensor model of the fermentation stage B at the moment $k+\tau+1$, $\Sigma_{k+1}{}^{-1}$ is an inverse of a measurement noise covariance matrix of the fermentation stage B at a moment $k+1$, $\hat{D}_{k+\tau+1}{}^{-1}$ is a difference covariance matrix between the fermentation stage A and the fermentation stage B at the moment $k+\tau 1$, and $\hat{d}_{k+\tau+1}$ is a parameter difference between the fermentation stage A and the fermentation stage B at the moment $k+\tau 1$.

A method for designing the cell concentration online soft sensor of the fermentation stage B based on a parameter estimation vector $\hat{\theta}_{k+\tau+1}$ and the gain matrix $\hat{H}_{k+\tau+1}$ of the cell concentration soft sensor model of the fermentation stage B in step S1043 includes:

step 1: initializing $\hat{d}_0$, $G_0$, and $Q_0$ at an initial moment of the fermentation stage B;

where $\hat{d}$ is a model parameter difference between the fermentation stage A and the fermentation stage B, $\hat{d}_0$ and $G_0$ are $(p_B+q_B)$-dimensional zero vectors, and $Q_0$ is a $(p_B+q_B)\times(p_B+q_B)$-dimensional zero matrix;

step 2: solving the cell concentration online soft sensor of the fermentation stage B, specifically denoted as follows:

$$\hat{\theta}_{k+\tau+1}=\hat{\theta}_A+P_{k+\tau+1}G_{k+\tau+1},$$

where $$F_{k+\tau+1}=F_{k+\tau}+\sigma_{k+1}{}^{-2}x_{k+\tau+1}x_{k+\tau+1}{}^T=Q_{k+\tau}+f_{k+\tau+1},$$

$$G_{k+\tau+1}=G_{k+\tau}+\sigma_{k+\tau+1}{}^{-2}x_{k+\tau+1}(y_{k+\tau+1}-x_{k+\tau+1}{}^T\hat{\theta}_A)=G_{k+\tau}+g_{k+\tau+1},$$

$$P_{k+\tau+1}=(F_{k+\tau+1}+\hat{D}_{k+\tau+1}{}^{-1})^{-1},$$

$\hat{\theta}_A$ is the parameter estimation of the fermentation stage A, $\hat{\theta}_{k+\tau+1}$ is the parameter estimation of the fermentation stage B at the moment $k+\tau 1$, $\sigma_{k+\tau+1}{}^{-2}$ is a measurement noise variance of a cell concentration of the fermentation stage B at the moment $k+\tau 1$, $x_{k+\tau+1}$ is an input vector of the fermentation stage B at the moment $k+\tau 1$, $y_{k+\tau+1}$ is a cell concentration of the fermentation stage B at the moment $k+\tau 1$, and when new measurement data is acquired, $F_{k+\tau+1}$ has updated data quality of the fermentation stage B, and $G_{k+\tau+1}$ and $P_{k+\tau+1}$ have updated a difference between the fermentation stages A and B; and step 3: before the fermentation stage B ends, when new measurement data is acquired, sequentially calculating $F_{k+\tau+1}$, $G_{k+\tau+1}$, and $P_{k+\tau+1}$, and updating a parameter $\hat{\theta}_{k+\tau+1}$ of the soft sensor model.

The method of minimizing the loss function in step S1042 is any one of a feasible direction method, a quadratic programming method, a particle swarm algorithm, Bayesian optimization, and a random search and gradient descent method.

A method for calculating the inverse of the noise covariance matrix in step S1042 is any one of a Kalman filter and an extended form thereof, statistical hypothesis testing, and regression analysis.

A method for calculating the model parameter difference d between the fermentation stage A and the fermentation stage B in step S1042 is any one of a recursive least squares method, a recursive extended least squares method, a recursive maximum likelihood method, a random Newton method, Kalman estimation, a prediction error method, and a long short-term memory network.

Furthermore, the method for predicting a cell concentration of the fermentation stage B according to the cell concentration soft sensor of the fermentation stage B in step S5 is:

introducing the parameter estimation $\hat{\theta}_{k+\tau+1}$ of the soft sensor into the soft sensor universal model $y_{k+\tau}=x_{k+\tau}{}^T\theta+v_{k+\tau}$, to obtain a predicted cell concentration value $\hat{y}_{k+\tau+1}$ of the fermentation stage B:

$$\hat{y}_{k+\tau+1}=x_{k+\tau+1}{}^T\hat{\theta}_{k+\tau+1}$$

where $\theta$ is a parameter of the universal model, $\hat{\theta}_{k+\tau+1}$ is the parameter estimation of the fermentation stage B at the moment $k+\tau 1$, $x_{k+\tau}$ is the input vector at the moment $k+\tau$, $V_{k+\tau}$ is the cell concentration measurement noise at the moment $k+\tau$, $\hat{y}_{k+\tau+1}$ is the predicted cell concentration value of the fermentation stage B at the moment $k+\tau+1$.

The performance of the online soft sensor designed above is verified below. An indicator for analyzing the performance of the soft sensor may be any one of a mean squared error, root mean squared error, a mean absolute error, a mean absolute percentage error, a mean squared error logarithm, and a median absolute error. The mean squared error (MSE) is selected as an evaluation indicator for recognition accuracy. It is defined that errors of the soft sensor model at the moments $k+\tau$ and $k+\tau 1$ are respectively $MSE(\hat{\theta}_{k+\tau})$ and $MSE(\hat{\theta}_{k+\tau+1})$.

$MSE(\hat{\theta}_{k+\tau+1})-MSE(\hat{\theta}_{k+\tau})=\text{trace}\{E[F_{k+\tau}+q_{k+\tau+1}+\hat{D}_{k+\tau+1}{}^{-1})^{-2}-(F_{k+\tau}+\hat{D}_{k+\tau+1}{}^{-1})^{-2}]\}<0$ is satisfied, indicating that as time elapses, an error of the value of the parameter estimation of the soft sensor model gradually decrease. The designed soft sensor has excellent performance.

Figure 6:
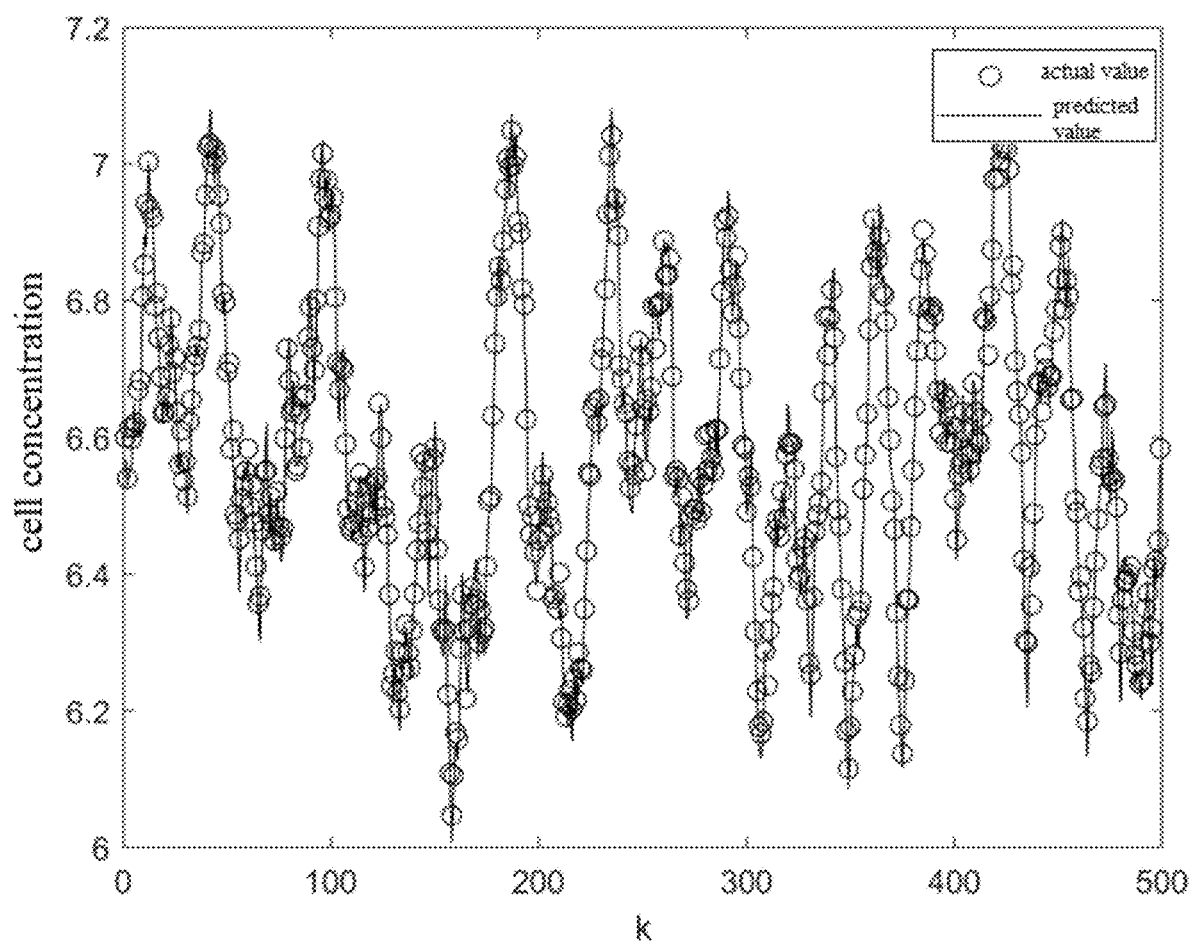
FIG. 6 shows an online predicted curve of a cell concentration of a fermentation stage B.

The cell concentration of the fermentation stage B is predicted according to the designed online soft sensor to obtain a predicted result of the cell concentration of the fermentation stage B, as shown in FIG. 6.

Embodiment 2

Figure 7:
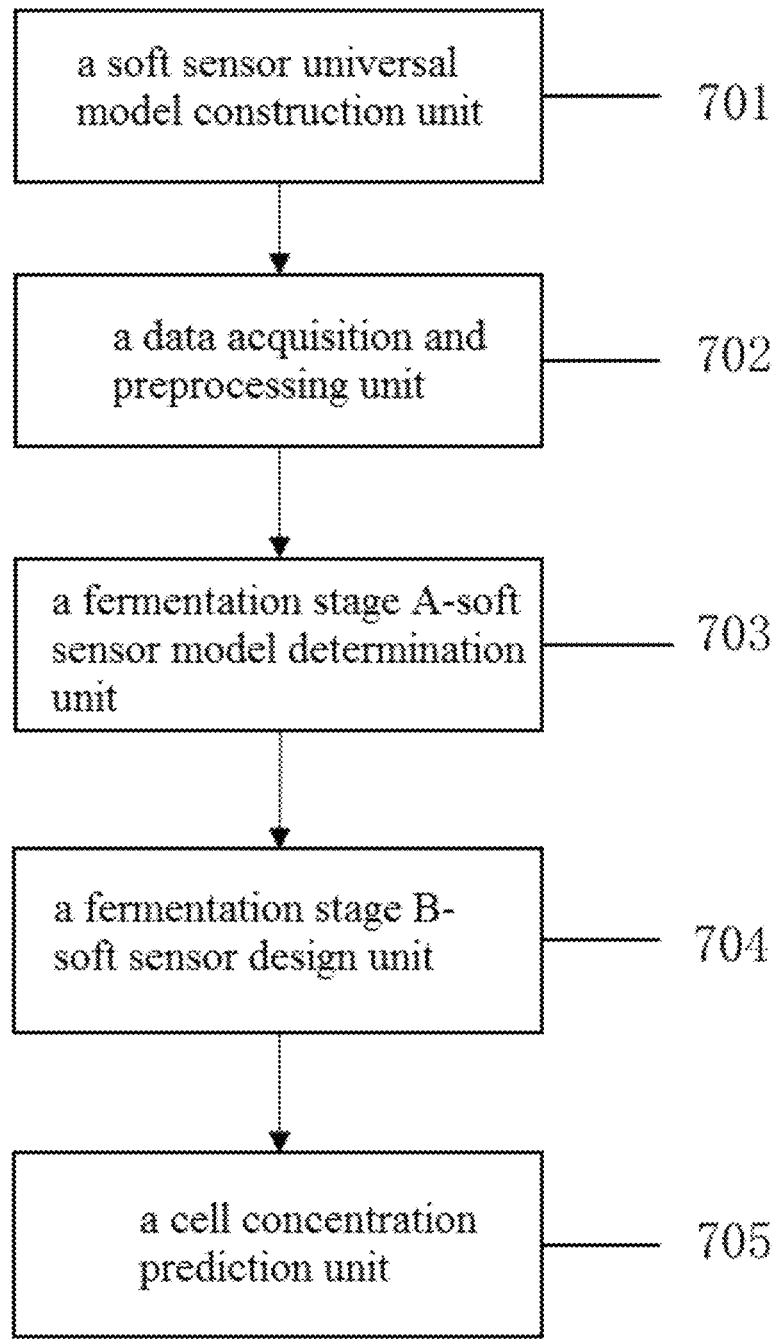
FIG. 7 is a block diagram of a knowledge reuse-based system for predicting a cell concentration in a fermentation process according to an embodiment of the present invention.

Embodiments of the present invention provide a knowledge reuse-based system for predicting a cell concentration in a fermentation process. As shown in FIG. 7, the system includes the following units:

a soft sensor universal model construction unit 701, configured to construct a cell concentration soft sensor universal model in a fermentation process, where the fermentation process is divided into four stages in time order: a lag phase, an exponential growth phase, a stationary phase, and a decline phase, and for two stages that occur successively, it is defined that a former stage is a fermentation stage A and a latter stage is a fermentation stage B;

a data acquisition and preprocessing unit 702, configured to acquire and preprocess process data of the fermentation stage A;

a fermentation stage A-soft sensor model determination unit 703, configured to determine a cell concentration soft sensor model of the fermentation stage A based on the cell concentration soft sensor universal model in combination with a process data result of the fermentation stage A after the preprocessing;

a fermentation stage B-soft sensor design unit 704, configured to acquire process data of the fermentation stage B, and after preprocessing, design a cell concentration online soft sensor of the fermentation stage B with the cell concentration soft sensor model of the fermentation stage A; and a cell concentration prediction unit 705, configured to predict a cell concentration of the fermentation stage B according to the cell concentration online soft sensor of the fermentation stage B.

The system is configured to implement the knowledge reuse-based method and system for predicting a cell concentration in a fermentation process in Embodiment 1 above. To avoid redundancy, details are not described again herein.

It should be noted that, the above description only provides preferred embodiments of the present invention and the employed technical principles. It should be appreciated by those skilled in the art that the present invention is not limited to the particular embodiments described herein. Those skilled in the art may make various obvious changes, readjustments, and replacements without departing from the scope of protection of the present invention. Therefore, while the present invention is illustrated in detail in combination with the above embodiments, the present invention is not only limited to the above embodiments, and can further include more other equivalent embodiments without departing from the concept of the present invention. The scope of the present invention is defined by the scope of the appended claims.

A person skilled in the art should understand that the embodiments of the present application may be provided as a method, a system or a computer program product. Therefore, the present application may use a form of hardware only embodiments, software only embodiments, or embodiments with a combination of software and hardware. Moreover, the present application may use a form of a computer program product that is implemented on one or more computer-usable storage media (including but not limited to a disk memory, a CD-ROM, an optical memory, and the like) that include computer usable program code.

The present application is described with reference to the flowcharts and/or block diagrams of the method, the device (system), and the computer program product according to the embodiments of the present application. It should be understood that computer program instructions may be used to implement each process and/or each block in the flowcharts and/or the block diagrams and a combination of a process and/or a block in the flowcharts and/or the block diagrams. These computer program instructions may be provided for a general-purpose computer, a dedicated computer, an embedded processor, or a processor of any other programmable data processing device to generate a machine, so that the instructions executed by a computer or a processor of any other programmable data processing device generate an apparatus for implementing a specific function in one or more processes in the flowcharts and/or in one or more blocks in the block diagrams.

These computer program instructions may be stored in a computer readable memory that can instruct the computer or any other programmable data processing device to work in a specific manner, so that the instructions stored in the computer readable memory generate an artifact that includes an instruction apparatus. The instruction apparatus implements a specific function in one or more processes in the flowcharts and/or in one or more blocks in the block diagrams. These computer program instructions may be loaded onto a computer or another programmable data processing device, so that a series of operations and steps are performed on the computer or the another programmable device, thereby generating computer-implemented processing. Therefore, the instructions executed on the computer or the another programmable device provide steps for implementing a specific function in one or more processes in the flowcharts and/or in one or more blocks in the block diagrams.

Obviously, the foregoing embodiments are merely examples for clear description, rather than a limitation to implementations. For a person of ordinary skill in the art, other changes or variations in different forms may also be made based on the foregoing description. All implementations cannot and do not need to be exhaustively listed herein. Obvious changes or variations that are derived there from still fall within the protection scope of the invention of the present invention.

What is claimed is:

1. A knowledge reuse-based method for predicting a cell concentration in a fermentation process, comprising:

S1: constructing a cell concentration soft sensor universal model in a fermentation process, wherein the fermentation process is divided into four stages in time order: a lag phase, an exponential growth phase, a stationary phase, and a decline phase, and for two stages that occur successively, it is defined that a former stage is a fermentation stage A and a latter stage is a fermentation stage B;

S2: acquiring and preprocessing process data of the fermentation stage A;

S3: determining a cell concentration soft sensor model of the fermentation stage A based on the cell concentration soft sensor universal model in combination with a process data result of the fermentation stage A after the preprocessing;

S4: acquiring process data of the fermentation stage B, and after preprocessing, designing a cell concentration online soft sensor of the fermentation stage B with the cell concentration soft sensor model of the fermentation stage A; and S5: predicting a cell concentration of the fermentation stage B according to the cell concentration online soft sensor of the fermentation stage B, wherein a method for designing a cell concentration online soft sensor of the fermentation stage B in step S4 is:

S41: setting a parameter estimation of the cell concentration soft sensor model of the fermentation stage B to:

$$\hat{\theta}_{k+\tau+1} = \hat{\theta}_A + \hat{H}_{k+\tau+1} E_{k+\tau+1},$$

wherein $$E_{k+\tau+1} = Y_{k+\tau+1} - X_{k+\tau+1} \hat{\theta}_A,$$

$$Y_{k+\tau+1} = [y_{1+\tau}, y_{2+\tau} \ldots, y_{k+\tau}, y_{k+\tau+1}]^T = [Y_{k+\tau}; y_{k+\tau+1}],$$

$$X_{k+\tau+1} = \begin{bmatrix} -y_\tau & \cdots & -y_{\tau-p} & u_1 & \cdots & u_{1-q} \\ -y_{1+\tau} & \cdots & -y_{1+\tau-p} & u_2 & \cdots & u_{2-q} \\ \vdots & \ddots & \vdots & \vdots & \ddots & \vdots \\ -y_{k-1+\tau} & \cdots & -y_{k-1+\tau} & u_k & \cdots & u_{k-q} \\ -y_{k+\tau} & \cdots & -y_{k+\tau-p} & u_{k+1} & \cdots & u_{k+1-q} \end{bmatrix} = [X_{k+\tau}; x_{k+\tau+1}^T],$$

wherein at a moment k+τ+1, for the cell concentration soft sensor model of the fermentation stage B, a delay is $\tau_B=\tau_A$, orders are $p_B=p_A$ and $q_B=q_A$, the parameter estimation is $\hat{\theta}_{k+\tau+1}=[\hat{a}, \cdots, \hat{a}_{p_B}, \hat{b}_1, \cdots, \hat{b}_{q_B}]^T$, $\hat{a}_1, \cdots, \hat{a}_{p_B}, \hat{b}_1, \cdots, \hat{b}_{q_B}$ is an estimate of each parameter in the parameter vector of the fermentation stage B at the moment k+τ+1, where a is a parameter of a autoregressive model and b is a parameter of a moving model, $\hat{\theta}_A$ is a parameter estimation of the fermentation stage A, $\hat{H}_{k+\tau+1}$ is a gain matrix of the cell concentration soft sensor model of the fermentation stage B at the moment k+τ+1, $E_{k+\tau+1}$ is an innovation vector at the moment k+τ+1, $Y_{k+\tau+1}$ is a cell concentration matrix of the fermentation stage B at the moment k+τ+1, and $X_{k+\tau+1}$ is an input matrix of the fermentation stage B at the moment k+τ+1;

S42: calculating the gain matrix $\hat{H}_{k+\tau+1}$ of the cell concentration soft sensor model of the fermentation stage B in step S41;

S43: designing the cell concentration online soft sensor of the fermentation stage B based on a parameter estimation vector $\hat{\theta}_{k+\tau+1}$ and the gain matrix $\hat{H}_{k+\tau+1}$ of the cell concentration soft sensor model of the fermentation stage B.

2. The knowledge reuse-based method for predicting a cell concentration in a fermentation process according to claim 1, wherein a method for constructing a cell concentration soft sensor universal model in a fermentation process in step S1 comprises:

S11: selecting a dilution ratio as an auxiliary variable based on dynamic characteristics of the fermentation process, and setting the cell concentration soft sensor model to:

$$y_{k+\tau}+a_1 y_{k+\tau-1}+\cdots+a_p y_{k+\tau-p}=b_0 u_k+b_1 u_{k-1}+\cdots+b_q u_{k-q}+v_{k+\tau},$$

wherein k is a moment, τ is the delay of the soft sensor model, p and q are the orders of the soft sensor model, a and b are coefficients, $y_{k+\tau}$ is a cell concentration at a moment k+τ, $u_k$ is an auxiliary variable at the moment k, $v_{k+\tau}$ is a cell concentration measurement noise at the moment k+τ, and a type of the noise is selected from white noises satisfying Gaussian distribution, t distribution, and Poisson distribution; and S12: performing vector transformation on the cell concentration soft sensor model, to obtain the cell concentration soft sensor universal model:

$$y_{k+\tau}=x_{k+\tau}^T \theta + v_{k+\tau},$$

wherein an input vector is $x_{k+\tau}=[y_{k+\tau-1}\ y_{k+\tau-2}\ \cdots\ y_{k+\tau-p}\ u_k\ \cdots\ u_{k-q}]^T$, and a parameter is $\theta=[a_1, \cdots, a_p, b_0, \cdots, b_q]^T$.

3. The knowledge reuse-based method for predicting a cell concentration in a fermentation process according to claim 1, wherein a method for preprocessing process data of the fermentation stage A in step S2 is:

eliminating a nonnumerical sample point in the process data of the fermentation stage A, and eliminating abnormal working condition data according to a working condition record; eliminating an outlier in the process data of the fermentation stage A; filling a missing value in the process data of the fermentation stage A; and removing a dimensional difference between an auxiliary variable and a quality variable in the fermentation stage A.

4. The knowledge reuse-based method for predicting a cell concentration in a fermentation process according to claim 1, wherein a method for calculating the gain matrix $\hat{H}_{k+\tau+1}$ of the cell concentration soft sensor model of the fermentation stage B in step S42 comprises:

step 1: defining a loss function of a knowledge reuse-based soft sensor model:

$$J=\text{trace}\{E[(\theta_B-\hat{\theta}_{k+\tau+1})(\theta_B-\hat{\theta}_{k+\tau+1})^T]\},$$

wherein $\theta_B$ is an actual parameter value of the fermentation stage B, $\hat{\theta}_{k+\tau+1}$ is the parameter estimation of the fermentation stage B at the moment k+τ+1, E[·] is an averaging operation, trace{·} is a trace operation of a matrix, J is a loss function with respect to $\hat{H}^{k+\tau+1}$; and step 2: calculating the gain matrix $\hat{H}_{k+\tau+1}$ based on a method of minimizing the loss function:

$$\hat{H}_{k+\tau+1}=(F_{k+\tau+1}+\hat{D}_{k+\tau+1}^{-1})^{-1} X_{k+1}^T \Sigma_{k+1}^{-1},$$

wherein $F_{k+\tau+1}=X_{k+1}^T \Sigma_{k+\tau+1}^{-1} X_{k+1}$, $\hat{D}_{k+\tau+1}^{-1}=\hat{d}_{k+\tau+1} \hat{d}_{k+\tau+1}^T$, $$X_{k+1}^T \hat{d}_{k+\tau+1}=E_{k+\tau+1},$$

$F_{k+\tau+1}$ is a Fisher information matrix of the soft sensor model of the fermentation stage B at the moment k+τ+1, $\Sigma_{k+1}^{-1}$ is an inverse of a measurement noise covariance matrix of the fermentation stage B at a moment k+1, $\hat{D}_{k+\tau+1}^-$ is a difference covariance matrix between the fermentation stage A and the fermentation stage B at the moment k+τ+1, and $\hat{d}_{k+\tau+1}$ is a parameter difference between the fermentation stage A and the fermentation stage B at the moment k+τ+1.

5. The knowledge reuse-based method for predicting a cell concentration in a fermentation process according to claim 1, wherein a method for designing the cell concentration online soft sensor of the fermentation stage B based on a parameter estimation vector $\hat{\theta}_{k+\tau+1}$ and the gain matrix $\hat{H}_{k+\tau+1}$ of the cell concentration soft sensor model of the fermentation stage B in step S43 comprises:

step 1: initializing $\hat{d}_0$, $G_0$, and $Q_0$ at an initial moment of the fermentation stage B;

wherein $\hat{d}$ is a model parameter difference between the fermentation stage A and the fermentation stage B, $\hat{d}_0$ and $G_0$ are $(p_B+q_B)$-dimensional zero vectors, and $Q_0$ is a $(p_B+q_B)\times(p_B+q_B)$-dimensional zero matrix;

step 2: solving the cell concentration online soft sensor of the fermentation stage B, specifically denoted as follows:

$$\hat{\theta}_{k+\tau+1}=\hat{\theta}_A+P_{k+\tau+1}G_{k+\tau+1},$$

where $$F_{k+\tau+1}=F_{k+\tau}+\sigma_{k+1}^{-2}x_{k+\tau+1}x_{k+\tau+1}^T=Q_{k+\tau}+f_{k+\tau+1},$$

$$G_{k+\tau+1}=G_{k+\tau}+\sigma_{k+\tau+1}^{-2}x_{k+\tau+1}(y_{k+\tau+1}-x_{k+\tau+1}^T\hat{\theta}_A)=G_{k+\tau}+g_{k+\tau+1},$$

$$P_{k+\tau+1}\leq(F_{k+\tau+1}+\hat{D}_{k+\tau+1}^{-1})^{-1},$$

$\hat{\theta}_A$ is the parameter estimation of the fermentation stage A, $\hat{\theta}_{k+\tau+1}$ is the parameter estimation of the fermentation stage B at the moment k+τ+1, $\sigma_{k+\tau+1}^{-2}$ is a measurement noise variance of a cell concentration of the fermentation stage B at the moment k+τ+1, $x_{k+\tau+1}$ is an input vector of the fermentation stage B at the moment k+τ+1, $y_{k+\tau+1}$ is a cell concentration of the fermentation stage B at the moment k+τ+1, and when new measurement data is acquired, $F_{k+\tau+1}$ has updated data quality of the fermentation stage B, and $G_{k+\tau+1}$ and $P_{k+\tau+1}$ have updated a difference between the fermentation stages A and B; and step 3: before the fermentation stage B ends, when new measurement data is acquired, sequentially calculating $F_{k+\tau+1}$, $G_{k+\tau+1}$, and $P_{k+\tau+1}$, and updating a parameter $\hat{\theta}_{k+\tau+1}$ of the soft sensor model.

6. The knowledge reuse-based method for predicting a cell concentration in a fermentation process according to claim 2, wherein a method for predicting a cell concentration of the fermentation stage B according to the cell concentration online soft sensor of the fermentation stage B in step S5 comprises:

introducing the parameter estimation $\hat{\theta}_{k+\tau+1}$ of the soft sensor into the soft sensor universal model $y_{k+\tau} = x_{k+\tau}^T \theta + v_{k+\tau}$, to obtain a predicted cell concentration value $\hat{y}_{k+\tau+1}$ of the fermentation stage B:

$$\hat{y}_{k+\tau+1} = x_{k+\tau+1}^T \hat{\theta}_{k+\tau+1},$$

wherein $\theta$ is a parameter of the universal model, $\hat{\theta}_{k+\tau+1}$ is the parameter estimation of the fermentation stage B at the moment k+τ+1, $x_{k+\tau}$ is the input vector at the moment k+τ, $v_{k+\tau}$ is the cell concentration measurement noise at the moment k+τ, $\hat{y}_{k+\tau+1}$ is the predicted cell concentration value of the fermentation stage B at the moment k+τ+1.

7. The knowledge reuse-based method for predicting a cell concentration in a fermentation process according to claim 4, wherein the method of minimizing the loss function is selected from a feasible direction method, a quadratic programming method, a particle swarm algorithm, Bayesian optimization, and a random search and gradient descent method.

8. The knowledge reuse-based method for predicting a cell concentration in a fermentation process according to claim 4, wherein a method for calculating the inverse of the noise covariance matrix is selected from a Kalman filter and an extended form thereof, statistical hypothesis testing, and regression analysis.

9. The knowledge reuse-based method for predicting a cell concentration in a fermentation process according to claim 4, wherein a method for calculating the model parameter difference $\hat{d}$ between the fermentation stage A and the fermentation stage B is selected from a recursive least squares method, a recursive extended least squares method, a recursive maximum likelihood method, a random Newton method, Kalman estimation, a prediction error method, and a long short-term memory network.

* * * * *